United States Patent
Guenther

(10) Patent No.: US 8,747,522 B2
(45) Date of Patent: Jun. 10, 2014

(54) METHOD FOR THE ADSORPTIVE DRYING OF PURIFIED BIOGAS AND FOR REGENERATING LADEN ADSORBENTS

(75) Inventor: Lothar Guenther, Geretsried (DE)

(73) Assignee: DGE Dr.-Ing. Guenther Engineering GmbH, Wittenberg (DE)

(*) Notice: Subject to any disclaimer, the term of this patent is extended or adjusted under 35 U.S.C. 154(b) by 0 days.

(21) Appl. No.: 13/634,326

(22) PCT Filed: Mar. 8, 2011

(86) PCT No.: PCT/EP2011/001116
§ 371 (c)(1),
(2), (4) Date: Sep. 12, 2012

(87) PCT Pub. No.: WO2011/110322
PCT Pub. Date: Sep. 15, 2011

(65) Prior Publication Data
US 2013/0000486 A1    Jan. 3, 2013

(30) Foreign Application Priority Data
Mar. 12, 2010 (DE) .................... 10 2010 011 347

(51) Int. Cl.
*B01D 53/04* (2006.01)
*B01D 53/26* (2006.01)

(52) U.S. Cl.
USPC ........ 95/99; 95/105; 95/120; 95/123; 95/124; 95/125

(58) Field of Classification Search
USPC ............. 95/14, 95–99, 105, 106, 117–120, 95/123–125; 96/112, 132
See application file for complete search history.

(56) References Cited

U.S. PATENT DOCUMENTS

| | | | | |
|---|---|---|---|---|
| 3,594,983 A | * | 7/1971 | Yearout | 95/97 |
| 4,581,044 A | * | 4/1986 | Uno et al. | 95/96 |
| 4,636,225 A | | 1/1987 | Klein et al. | |
| 4,784,672 A | * | 11/1988 | Sircar | 95/97 |
| 5,234,479 A | | 8/1993 | Henderson et al. | |
| 5,451,249 A | * | 9/1995 | Spiegel et al. | 95/117 |
| 8,460,434 B2 | * | 6/2013 | Turner et al. | 95/117 |
| 2010/0107872 A1 | | 5/2010 | Bethell | |
| 2012/0024157 A1 | * | 2/2012 | Maheshwary et al. | 96/133 |

FOREIGN PATENT DOCUMENTS

| | | |
|---|---|---|
| DE | 103 59 959 A1 | 7/2005 |
| EP | 0 207 277 A1 | 1/1987 |
| GB | 2 181 666 A | 4/1987 |
| JP | 2005/133939 A | 5/2005 |
| WO | 2008/115079 A1 | 9/2008 |
| WO | 2009/101669 A1 | 8/2009 |

\* cited by examiner

*Primary Examiner* — Frank Lawrence, Jr.
(74) *Attorney, Agent, or Firm* — Laurence A. Greenberg; Werner H. Stemer; Ralph E. Locher

(57) ABSTRACT

In a method for adsorptively drying purified biogas and regenerating laden absorbents, foreign matter is not allowed to enter the purified biogas, the content of methane in the gas remains virtually unchanged and the effort involved in regenerating the laden adsorbent is reduced. Drying and regeneration are effected in a closed biogas cycle, wherein separate layers based on silica gel and molecular sieves are used as the adsorbent. The biogas to be dried first flows through the silica gel layer. The adsorbent is regenerated with exclusively heated, dried biomethane having a temperature of up to 150° C. which, after contact with adsorbent, is recirculated to the outflow of purified biogas. After regeneration, the bed is cooled by biomethane, which is subsequently recirculated to the outflow of purified biogas. Methane-containing water accumulating during drying and regeneration is recirculated to the biogas generation and/or purification.

11 Claims, 1 Drawing Sheet

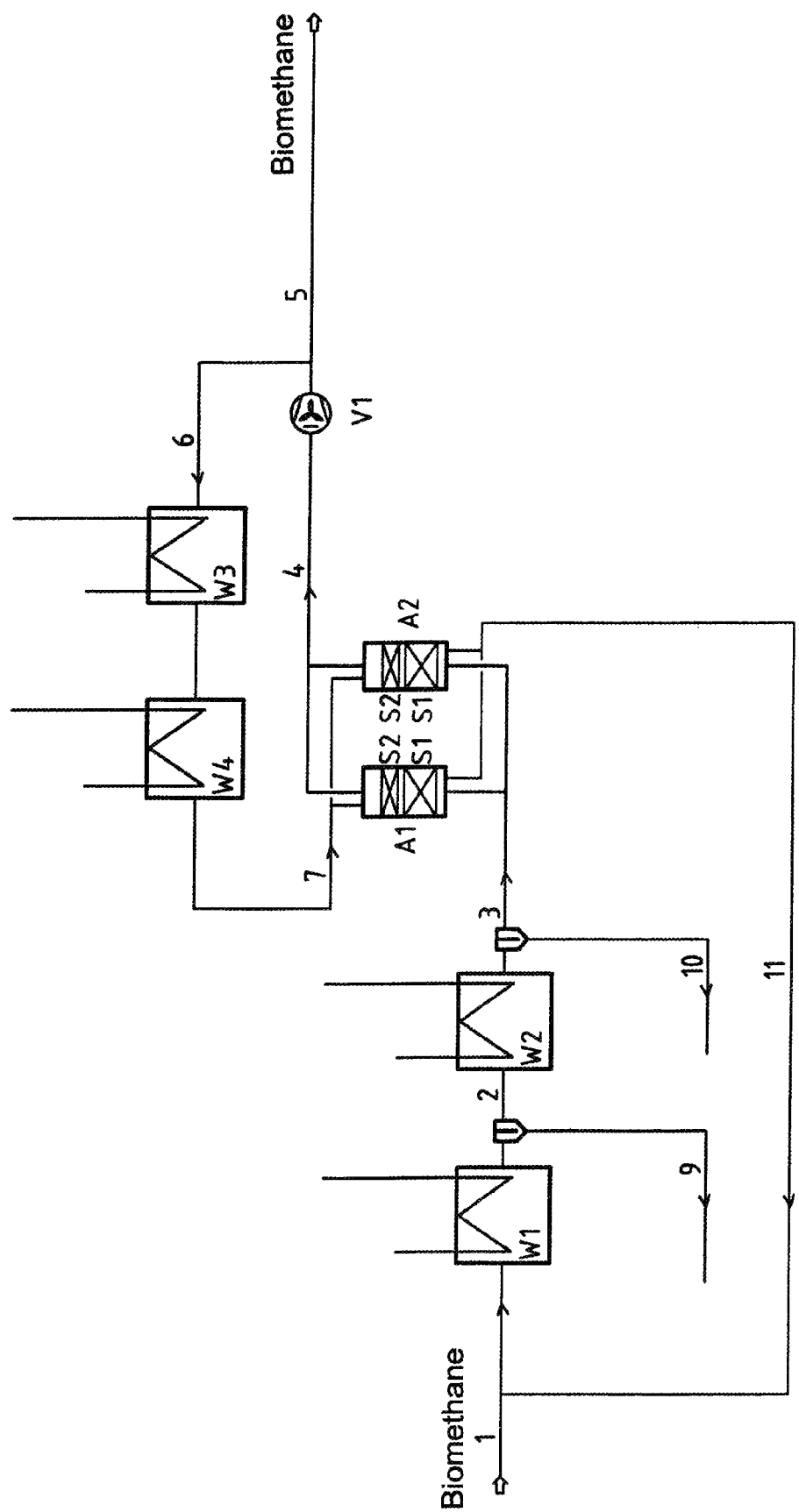

METHOD FOR THE ADSORPTIVE DRYING OF PURIFIED BIOGAS AND FOR REGENERATING LADEN ADSORBENTS

BACKGROUND OF THE INVENTION

Field of the Invention

The invention relates to a process for adsorptive drying of purified biogas (called biomethane) and regeneration of laden adsorbents, wherein the dried biogas is sent to a further use, for example by feeding into a conventional natural gas grid.

Biogas can be purified by different processes, with the aim of obtaining a gas with a relatively high proportion of methane, in the range from 90 to 99% by volume.

After the purification, biomethane may still comprise, as residual constituents, carbon dioxide (0.1 to 4% by volume), hydrogen (0.01 to 0.2% by volume), nitrogen and oxygen (0.2 to 4% by volume) and water (1 to 3% by volume). Further components, for example $H_2S$, $NH_3$, may still be present in the range from 1 to 5 ppm. Depending on the fermentation process, the purified biogas (biomethane) may still contain proportions of aromatic or other hydrocarbons, in amounts of up to 1000 ppm, with ignition points well below that of methane.

For a further use of biomethane, for example for feeding into a natural gas grid, it is necessary to remove water present in the gas down to a limit of below 40 mg/m$^3$ (STP).

For drying or demoisturization of biogas, processes for cooling and condensation and for adsorption and absorption are already known. The cooling is usually effected within underground pipes provided with a condensate separator at the lowest point. If required, water coolers can additionally be used. Adsorption processes are effected using specific adsorbents, such as activated carbon, molecular sieves or silica gel. After the loading, the adsorbents can be regenerated by heating.

Absorptive processes (EP 0 907 400 B1) work with a solvent such as triethylene glycol, and gas scrubbing results in dissolution of water present in the gas triethylene glycol, which can subsequently be regenerated again at a temperature of 200° C.

This procedure is very energy-intensive since water bound in the triethylene glycol has to be evaporated (distilled off). Since methane is soluble in triethylene glycol (approx. 30 g/l at 1 bar and 25° C.), methane losses have to be expected.

DE 103 59 959 B4 proposes using undried, moist biogas for regeneration of the moist triethylene glycol desiccant.

DE 20 2008 012 371 U1 discloses an apparatus for adsorptive drying of biogas in a fixed bed (molecular sieves), using electrodes which are connected to an HF generator for supply of HF voltage to heat the fixed bed. The additional heating of the solid bed by means of HF energy is associated with a high level of complexity. Moreover, there is a considerable safety risk since particular substances with a tendency to self-ignite may be present in the biogas or natural gas.

BRIEF SUMMARY OF THE INVENTION

It is an object of the invention to provide a process for adsorptive drying of purified biogas having a methane content of at least 90% by volume and regeneration of laden adsorbents, in which no extraneous substances can get into the purified biogas, the proportion of methane present in the gas to be purified remains present virtually unchanged, and the complexity for regeneration of the laden adsorbent is reduced.

According to the invention, the object is achieved by the features as claimed. Advantageous configurations and developments of the procedure are the subject to dependent claims.

For adsorptive drying of purified biogas (biomethane), the adsorbents used are separate layers based on silica gel and molecular sieves, the biogas to be dried flowing first through the silica gel layer. The layer of silica gel preferably consists of two layers, a lower macroporous layer and an upper mesoporous layer. A ratio between the lower layer to the upper layer lies between 1:1 and 1:4. The vol ime ratio of first "silica gel" layer to second "molecular sieves" layer is 20:1 to 3:1, preferably 12:1 to 8:1. This depends on the water content of the biogas to be dried (biomethane). The higher the water content in the biogas to be dried, the greater the ratio thereof.

The layer of silica gel may also be formed from at least two layers of different silica gels, the space between these two layers being heated by means of an external heat source. This can be accomplished by means of an installed intermediate heater.

This measure can achieve water contents in the biogas of below 10 mg/m$^3$ (STP) and dew points of −60° C. to −80° C.

The biogas to be dried is preferably pumped through the adsorber at ambient pressure. If required, a pressure of up to 1 bar can also be employed. Prior to the drying of the purified biogas (biomethane), the water content should already be reduced down to 5 g/m$^3$ (STP). This can be accomplished, for example, by cooling down to 10 to 30° C with cooled biomethane. Without prior drying, correspondingly greater dimensions of the adsorbers are required. The adsorption time is 12 to 14 hours. Within this time, the water content in the dried biomethane can be reduced down to well below 20 mg/m$^3$ (STP).

For subsequent regeneration of the adsorbent, exclusively heated dried biomethane is used, and this is recycled back into the starting stream of purified biogas after the contact with adsorbent. The heating is preferably effected to a temperature of approx. 110 to 150° C. in a separate heat exchanger by means of a heat carrier, such as thermal oil or hot water or steam. For this purpose, exact temperature control is required in order to avoid self-ignition of hydrocarbons present in the biomethane. The temperature of the heat carrier should not exceed 200° C. During the regeneration of the bed, the temperature of the exiting biomethane is measured continuously. During the regeneration, this is within a range from 20 to 30° C. If the exit temperature rises to 40 to 50° C., the supply of biomethane is shut down and the regeneration process is ended.

It is advantageous when the adsorber is heated at least in the lower region on commencement of the regeneration. This can be accomplished by means of a jacket or a heating coil through which a heat carrier medium flows. Additional heating of the adsorber during the first hour of regeneration is already sufficient.

The duration of indirect heating of the adsorber should be at least 30 minutes. The heat carrier medium should have an of temperature 70 to 180° C.

The areas to be heated should be at least 10% of the adsorber height.

Under these conditions, it was found that, for a given heat input, the drying time for the laden bed can be reduced by up to 50%. This is achieved, more particularly, by faster introduction of the heat required to heat the adsorbers than customary to date via the drying gas stream. Thus, the drying process proceeds much more effectively in the region of the macroporous silica gels, i.e. where the greatest amount of water is bound. The indirect heating of the adsorber during the drying step is required only over a period of up to 1 hour. Thereafter, the heating can be switched off.

For direct reuse of the adsorber for drying purified biogas (biomethane), cooling of the bed to standard temperature is required. For this purpose, purified biogas (biomethane) is used, which is cooled down to 5 to 15° C. in a separate heat exchanger and passed through the bed. After about two hours, the temperature of the bed is again within the desired range. The biomethane used for regeneration and cooling is sent back to the starting stream of purified biogas. In the individual process stages, predrying and regeneration, water obtained is collected and recycled back into the circuit for production and/or purification of biogas.

The advantage of the process proposed is that of a closed biogas circuit. Since the adsorbent is regenerated exclusively with purified biogas, absolutely no extraneous substances can get into the biomethane during the drying. The dried biomethane can thus be fed without any problem, if appropriate after a pressure increase, into a natural gas grid, or can be sent to another use. In the case of recycling of the condensate obtained during the drying into a preliminary stage for biogas production, there are no methane losses. This procedure is thus very economically viable. The selected combination of the composition of the adsorber bed, in terms of activity, is matched to the amount of water to be removed and the regeneration conditions. The water content in the purified biogas (biomethane) can thus be reduced from approx. 5 g/m$^3$ (STP) down to at least 10 mg/m$^3$ (STP) or even lower, and the duration up to maximum loading and the duration for a thermally gentle regeneration (temperature max. up to 150° C.) and cooling of the laden bed can be kept about the same. Under thermally more favorable conditions, indirect heating of the adsorber, the regeneration time for the laden adsorber column can be reduced even further.

The mass transfer which takes place during the loading, the transfer of the water from the biogas to the adsorbents, shifts until the end of the adsorber column is reached and there is breakthrough of the moist biogas, but this is ruled out in practice by an early termination. The bed of molecular sieves disposed at the end extends the active mass transfer zone. The water absorption proceeds at first through the silica gel up to equilibrium. The next layer of molecular sieves absorbs water more slowly, but the loading capacity increases overall and enables the attainment of the low residual water contents of approx. 10 mg/m$^3$ (STP). On attainment of this value, the drying is ended without reaching the upper limit in the absorption capacity. Only thus is sufficient regeneration of the molecular sieves enabled at comparatively low temperatures (max. up to 150° C.). Higher regeneration temperatures would be prevented by the use of biomethane due to the self-ignition risk.

Application of a reduced pressure during the regeneration allows the removal of water to be improved, and may make it possible to work at lower regeneration temperatures.

The invention is illustrated hereinafter by two examples. The accompanying drawing shows the function circuit diagram of a plant for performance of the process.

BRIEF DESCRIPTION OF THE EXAMPLES

Example 1

A: Drying

Biogas produced from biological waste material in a fermenter is purified to free it of unwanted secondary constituents, with removal of carbon dioxide present by means of an ambient pressure amine scrubbing. From the scrubbing column, 30 m$^3$ (STP)/h of purified biogas, called biomethane, are drawn off at a temperature of 38° C. The biomethane has the following composition:

| | |
|---|---|
| $CH_4$ | 95.2% by vol. |
| $CO_2$ | 0.5% by vol. |
| $H_2O$ | 4.0% by vol. |
| $O_2$ | 0.1% by vol. |
| $N_2$ | 0.2% by vol. |
| $H_2S$ | 2 ppm |
| $NH_3$ | 1 ppm |

The biomethane drawn off via line 1 is cooled in a first heat exchanger W1 to approx. 22° C. and then passed via line 2 to the downstream, second heat exchanger W2 and cooled therein down to 5° C. This reduces the water content in the biomethane from originally 19 500 mg/m$^3$ (STP) down to 5035 mg/m$^3$ (STP). Via lines 9 and 10, separated water is removed to a non-illustrated vessel, optionally stored intermediately, and sent back to the biogas production or purification.

The amount of biomethane is reduced to 28.99 m$^3$ (STP)/h. The composition of the biomethane removed via line 3 has changed as follows:

| | |
|---|---|
| $CH_4$ | 98.52% by vol. |
| $CO_2$ | 0.52% by vol. |
| $H_2O$ | 0.66% by vol. |

To dry the biomethane, two identical adsorbers A1 and A2 with a bed height of 700 mm and a diameter of 300 mm, arranged downstream, are used alternately for drying of the biomethane and, after loading, subjected to a regeneration. While one adsorber is in drying operation, the other adsorber is being regenerated.

Both adsorbers A1 and A2 contain a loose bed consisting of two different adsorbents S1 and S2. The lower bed S1 consists of 20 l of silica gel with a mean pore diameter of >50 to 100 nm (macropores) and 30 l of silica gel with a mean pore diameter of 25 nm (mesopores), which are separated by a gas-permeable plate. The orifices in the plate are so small that mixing of different silica gel particles is impossible.

Above the mesoporous silica gel bed is disposed a bed S2 of molecular sieves (zeolites) with a pore diameter of 0.4 nm, in an amount of 5 l. The silica gel bed and the molecular sieves are separated by a gas-permeable plate, such that the particles cannot mix. The ratio of bed S1:bed S2 is 50:5=10.

In continuous operation, the biomethane is supplied via line 3 to one of the two adsorbers A1 or A2, for example to adsorber A1, and is dried during contact with the adsorbents. At the same time, i.e. in parallel, the other adsorber A2, which has been laden in the meantime, is regenerated.

After leaving the second heat exchanger W2 at a temperature of 5° C., the biomethane to be dried flows from the bottom through the bed in the adsorber column A1 and is drawn off at the top of the adsorber A1 via line 4. The drying is in principle effected at ambient pressure; only the suction pressure for conveying the gas stream is applied, and this is approx. 10 mbar.

According to the specific application, the dimensions of the adsorber column and the flow rate are determined experimentally, with consideration of maximum effectiveness of the mass transfer zone.

The specific selection and composition of the adsorbents enables a relatively long utilization time. Only after an adsorption time of 14 hours is there breakthrough of the moist gas with the consequence of diversion of the gas stream to the other adsorber column 2 which has been regenerated in the meantime. During the first 14 hours of the adsorption, the water content in the dried biomethane is only 10 mg/m$^3$ (STP) (dew point −63° C.). The dried biomethane drawn off after compression via line 5 (temperature approx. 25° C.) can be fed directly into a natural gas grid.

If the adsorption time were to be prolonged by approx. 1 hour to 15 hours, the water content in the dried biomethane increases up to 153 mg/m$^3$ (STP) (dew point −40° C.).

B: Regeneration

During the drying of the biomethane which takes place in one adsorber column A1, the laden adsorber column A2 is regenerated as follows:

Downstream of the compressor V1, a closable branch line 6 is incorporated into the line 4 for removal of the dried biomethane, and this can be used to separate out 5 m$^3$/h of dried biomethane. This substream is passed through a third heat exchanger W3 and heated up to a temperature of approx. 120° C. and passed through line 7 to the adsorber to be regenerated. The hot substream of dried biomethane, for regeneration of the adsorber particles, is passed from the top through the laden adsorber column A2 and absorbs the moisture present in these particles while being cooled. The substream determined for the regeneration is pumped through the adsorber column at a pressure of 40 mbar.

After a regeneration time of approx. 12 hours, the adsorber bed again has sufficient loading capacity. The moisture-laden biomethane is sent back to the biomethane gas stream to be dried in the circuit.

For direct reuse of the adsorber bed for drying, however, cooling of the adsorbents is still required. For this purpose, the dried biomethane separated out via line 6 is not heated but passed directly through a fourth heat exchanger W4 and cooled therein to approx. 10° C., and passed through the bed in the adsorber A2. The cooled biomethane is transported via line 7. The biomethane used for cooling is recycled via line 11 back into the biomethane circuit. A cooling time of 2 hours is followed by switching from adsorber A1 to adsorber A2. The laden adsorber A1 is now regenerated and the adsorber A2 is used for drying.

Based on the starting amount of biomethane to be dried (approx. 30 m$^3$ (STP)/h), 1.2 l/h of water with a methane content of 28 g/l are discharged via lines 9 and 10. The water can be collected and then sent directly back to the biogas purification as scrubbing water. The amount of methane present in the condensate is 0.034 kg/h or 0.024 m$^3$ (STP)/h. This corresponds to a proportion of 0.084% of the amount of methane to be dried. The advantage of this procedure is that no methane losses occur.

In the case of plants with drying of approx.
5000 m$^3$ (STP)/h of methane, there would otherwise be methane losses amounting to 4 m$^3$ (STP)/h.

Example 2

The regeneration of the laden adsorber column is conducted under the same conditions as in example 1, with additional heating, during the first hour, of the lower section (up to a height of approx. 300 mm) of the adsorber column with a liquid heat carrier having a temperature of 150° C. At the same time, as in example 1, 5 m$^3$/h of dried biomethane at a temperature of approx. 120° C. and a pressure of 40 mbar are passed through the bed of the adsorber column.

The indirect additional heating accelerates the drying process for the silica gel bed which comprises the greater proportion of water or moisture.

Since the heating of the adsorber column already drives out a portion of the moisture present in the silica gel, the heat present in the drying gas (biomethane) can thus be utilized more effectively for the further drying of the bed, since the adsorber is already heated by the indirect heating in the region where the greatest proportion of moisture is present.

After a drying time of approx. 8 hours, the adsorber bed has again attained adequate loading capacity and is cooled for another two hours in an analogous manner to that in the example. After 10 hours of regeneration, the adsorber bed is again fully usable. In the case of subsequent use of the adsorber column, it was found that the bed has a much higher loading capacity compared to example 1.

During the first 14 hours of the adsorption of the biogas to be dried, the water content in the dried biomethane is only 4 mg/m$^3$ (STP) (dew point −70° C.). In the case of extension of the adsorption time by approx. 1 hour to 15 hours, the water content in the dried biomethane increases up to 10 mg/m$^3$ (STP) (dew point −63° C.).

This example shows that, in the case of use of indirect adsorber heating, much better drying can be achieved with lower water contents and a shorter drying time.

Example 3

Under the same conditions as in example 2, the regeneration temperature is now increased from 120 to 140° C.

Under these conditions, the water content in the dried biomethane up to 10 hours is 50 to 80 mg/m$^3$ (STP), then it rises to 160 mg/m$^3$ (STP) within 1 hour.

This shows that, in spite of higher energy expenditure of example 2, only a small improvement in the drying can be achieved. In the case of use of higher regeneration temperatures, the adsorber bed is damaged. An increase in the drying gas rate via line 4 from 5 to 10 m$^3$ (STP)/h reduces the water content in the dried biomethane to 40 to 70 mg/m$^3$ (STP) over the first 10 hours, but requires twice the regeneration power.

DESCRIPTION OF THE INVENTION

Comparative Example 1

In contrast to example 1, the moist biomethane is dried using only one bed consisting of 55 l of silica gel with a pore diameter of 25 nm.

Under the same conditions as in example 1, breakthrough of the moist gas occurs after an adsorption time of only 10 hours.

In the dried biomethane, a residual water content of 100 to 120 mg/m$^3$ (STP) is found over the adsorption time.

Comparative Example 2

Under the same conditions as in example 2, the desiccant used is now 20 l of silica gel with a pore diameter of 50-100 nm followed above by only 35 l of silica gel with a pore diameter of 25 nm.

Under these conditions, the water content in the dried biomethane is 40 to 50 mg/m$^3$ (STP) up to 12 hours, then it rises to 145 mg/m$^3$ (STP) within 1 hour.

The invention claimed is:
1. A gas drying process, comprising:
providing a purified biogas having a methane content of at least 90% by volume;

providing an adsorber with adsorbents in the form of separate layers based on silica gel and molecular sieves;

adsorptively drying the purified biogas with the adsorbents and regenerating laden adsorbents in a closed biogas circuit; and conducting the biogas to be dried first through a layer of silica gel, and wherein regenerating further comprises regenerating the adsorbent using exclusively heated dried biomethane having a temperature of up to 150° C. and, after contact with the adsorbent, recycling the biomethane back into a starting stream of the purified biogas; and on completion of regeneration, contacting cooled dried biomethane with the adsorbent and recycling back into the starting stream of the purified biogas, and conducting methane-containing water obtained during the drying and regeneration back to a biogas production and/or purification.

2. The process according to claim 1, which comprises removing a portion of water by cooling the purified biogas prior to supplying the purified biogas to the adsorber.

3. The process according to claim 1, wherein the layer of silica gel is formed from at least two layers including a lower macroporous layer and an upper mesoporous layer, with a volume ratio between the lower layer to the upper layer lying between 1:1 and 1:4.

4. The process according to claim 1, which comprises passing the biomethane for the regeneration through a bed of the adsorbent at a temperature of 110 to 150° C., with a continuous measurement of the temperature of the exiting biomethane, and a shutdown of a supply of biomethane after a rise in the exit temperature to 40 to 50° C.

5. The process according to claim 1, which comprises pumping the biogas to be dried through the adsorber at ambient pressure or with a slightly elevated pressure of up to 1 bar.

6. The process according to claim 1, wherein a volume ratio of a first layer being the silica gel layer to a second layer being the molecular sieves is 20:1 to 3:1.

7. The process according to claim 1, which comprises carrying out the adsorption during an adsorption time between 12 and 14 hours and thereby reducing a water content in the dried biomethane to below 20 mg/m$^3$ (STP).

8. The process according to claim 1, which comprises cooling the regenerated adsorbents, prior to reuse, down to 10 to 30° C. with cooled biomethane.

9. The process according to claim 8, which comprises cooling the regenerated adsorbents with cooled biomethane having a temperature of between 5 and 15° C.

10. The process according to claim 1, which comprises indirectly heating at least a lower region of the adsorber during the regeneration.

11. The process according to claim 1, which comprises regenerating the laden adsorber under reduced pressure.

* * * * *